United States Patent
Piermarini et al.

(10) Patent No.: US 10,433,554 B2
(45) Date of Patent: Oct. 8, 2019

(54) DEODORIZING COMPOUNDS, COMPOSITIONS, AND METHODS FOR REPELLING INSECTS

(71) Applicants: Ohio State Innovation Foundation, Columbus, OH (US); William L. Marr, Youngstown, OH (US)

(72) Inventors: Peter Marc Piermarini, Columbus, OH (US); William L. Marr, Youngstown, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 0 days.

(21) Appl. No.: 15/967,921

(22) Filed: May 1, 2018

(65) Prior Publication Data

US 2018/0310563 A1 Nov. 1, 2018

Related U.S. Application Data

(60) Provisional application No. 62/492,531, filed on May 1, 2017.

(51) Int. Cl.
| | |
|---|---|
| A01N 43/84 | (2006.01) |
| A01N 33/10 | (2006.01) |
| A01N 33/12 | (2006.01) |
| A01N 37/04 | (2006.01) |
| A01N 37/44 | (2006.01) |

(52) U.S. Cl.
CPC ............ *A01N 43/84* (2013.01); *A01N 33/10* (2013.01); *A01N 33/12* (2013.01); *A01N 37/04* (2013.01); *A01N 37/44* (2013.01)

(58) Field of Classification Search
CPC ........ A01N 33/10; A01N 37/04; A01N 37/44; A01N 43/84
See application file for complete search history.

(56) References Cited

U.S. PATENT DOCUMENTS

| | | | |
|---|---|---|---|
| 2,852,434 A | 9/1958 | Walters et al. | |
| 4,851,214 A | 7/1989 | Walters et al. | |
| 5,180,749 A | 1/1993 | Cusack et al. | |
| 5,489,433 A * | 2/1996 | Aboud .................. | A01N 37/36 424/405 |
| 6,664,254 B1 | 12/2003 | Rogozinski | |
| 9,451,763 B2 | 9/2016 | Daigle et al. | |
| 2007/0155628 A1* | 7/2007 | Pazhianur ............. | A01N 25/30 504/116.1 |
| 2008/0188456 A1* | 8/2008 | Bernier ................. | A01N 43/36 514/212.01 |
| 2016/0376263 A1 | 12/2016 | Patron et al. | |
| 2017/0028092 A1 | 2/2017 | Samani | |
| 2017/0290343 A1 | 10/2017 | Acosta | |

FOREIGN PATENT DOCUMENTS

| | | |
|---|---|---|
| WO | 0160373 | 8/2001 |
| WO | 200207707 | 1/2002 |
| WO | 2007120665 | 10/2007 |
| WO | 2009085889 | 7/2009 |
| WO | 2012054107 | 4/2012 |
| WO | 2013188183 | 12/2013 |
| WO | 2015042020 | 3/2015 |
| WO | 2015168658 | 11/2015 |
| WO | 2016131134 | 8/2016 |
| WO | 2016146671 | 9/2016 |
| WO | 2017058594 | 4/2017 |

\* cited by examiner

*Primary Examiner* — Sarah Pihonak
(74) *Attorney, Agent, or Firm* — Meunier Carlin & Curfman LLC

(57) ABSTRACT

The present disclosure relates to deodorizing compounds and compositions for use in methods of repelling insects and methods of reducing or preventing the transmission of mosquito-borne pathogens.

6 Claims, 1 Drawing Sheet

DEODORIZING COMPOUNDS, COMPOSITIONS, AND METHODS FOR REPELLING INSECTS

CROSS REFERENCE TO RELATED APPLICATIONS

This application claims the benefit of U.S. Provisional Patent Application Ser. No. 62/492,531 filed May 1, 2017, the disclosure of which is expressly incorporated herein by reference.

FIELD

The present disclosure relates to deodorizing compounds and compositions for use in methods of repelling insects and methods of reducing or preventing the transmission of mosquito-borne pathogens.

BACKGROUND

Mosquitoes are vectors of several medically-important arboviruses and parasites that are currently emerging and/or re-emerging around the globe. The diseases caused by these pathogens include, for example, dengue fever, chikungunya fever, malaria, yellow fever, and Zika virus. Vaccines for these diseases have not been developed (e.g., Zika), are not widely-available (e.g., dengue), or are limited in their supply (e.g., yellow fever). Thus, avoiding mosquito bites is the primary strategy to preventing transmission of these diseases.

While the application of insecticides and elimination of larval breeding sites are key components to managing mosquito populations, the use of repellents provides an important level of personal protection to minimize the chances of mosquito bites. However, the list of EPA-registered repellents that are recommended by the CDC for preventing mosquito bites is currently limited to N,N-Diethyl-meta-toluamide (DEET), picaridin, para-methane-diol (oil of lemon eucalyptus), and IR3535. Moreover, DEET, which is considered the "gold standard" for a repellent, has some important drawbacks. For example, DEET can dissolve plastics and mosquitoes can also become resistant to it. What is needed are new compounds, compositions, and methods to increase the diversity of active ingredients for developing novel mosquito repellents in order to help limit the spread of mosquito-borne diseases.

The compounds, compositions, and methods disclosed herein address these and other needs.

SUMMARY

Disclosed herein are compounds, compositions, and methods for using deodorizing compounds and compositions for repelling insects. In some embodiments, the inventors found that the deodorizing compositions PTG-MSQ$^{100}$, PTG-MSQ$^{200}$, and Ordenone® could mask human odors and prevent mosquito bites.

In one aspect, disclosed herein is a method of repelling an insect, comprising applying to a subject a composition in an amount effective to repel said insect; wherein said composition is selected from PTG-MSQ$^{100}$, PTG-MSQ$^{200}$, Ordenone®, or mixtures thereof.

In one aspect, disclosed herein is a method of repelling an insect, comprising applying to a subject a composition in an amount effective to repel said insect; wherein said composition is selected from:

i) a composition according to Formula I:

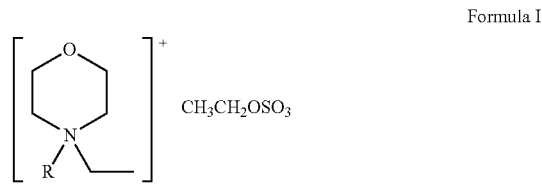

Formula I wherein R comprises a mixture of $C_{16}$-$C_{18}$ unsubstituted alkyl and $C_{16}$-$C_{18}$ unsubstituted alkenyl groups;

ii) a composition comprising betaine, sodium citrate, isopropylamine dodecylbenzene sulfonate, alcohol ethoxylate, and water;

iii) a composition comprising a water-based deodorizing agent having semi-rigid, concave molecular structures which capture odor-causing molecules;

or mixtures thereof.

In some embodiments, the composition is PTG-MSQ$^{100}$ which is a composition according to Formula I:

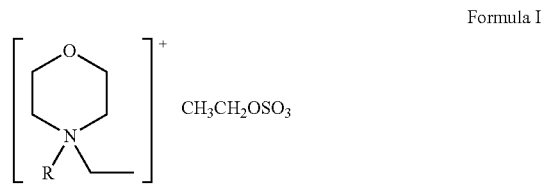

Formula I wherein R comprises a mixture of $C_{16}$-$C_{18}$ unsubstituted alkyl and $C_{16}$-$C_{18}$ unsubstituted alkenyl groups.

In some embodiments, the PTG-MSQ$^{100}$ composition is used at a concentration of 0.1-50%. In some embodiments, the PTG-MSQ$^{100}$ composition is used at a concentration of 1-15%. In some embodiments, the PTG-MSQ$^{100}$ composition is used at a concentration of 3-9%.

In some embodiments, the composition is PTG-MSQ$^{200}$, which is a composition comprising betaine, sodium citrate, isopropylamine dodecylbenzene sulfonate, alcohol ethoxylate, and water.

In some embodiments, the PTG-MSQ$^{200}$ composition is used at a concentration of 0.1-50%. In some embodiments, the PTG-MSQ$^{200}$ composition is used at a concentration of 1-50%. In some embodiments, the PTG-MSQ$^{200}$ composition is used at a concentration of 3-40%.

In some embodiments, the composition is Ordenone®, which is a composition comprising a water-based deodorizing agent having semi-rigid, concave molecular structures which capture odor-causing molecules.

In some embodiments, the Ordenone® composition is used at a concentration of 0.1-50%. In some embodiments, the Ordenone® composition is used at a concentration of 1-20%. In some embodiments, the Ordenone® composition is used at a concentration of 10%. In some embodiments, the Ordenone® composition is used at a concentration of about 10%.

In some embodiments, the insect (for example, an arthropod) is selected from the group consisting of mosquitoes, fleas, and ticks. In some embodiments, the insect is a mosquito. In some embodiments, the mosquito is selected from an *Aedes, Culex,* or *Anopheles* mosquito.

In some embodiments, the subject is a human. In some embodiments, the composition is in a spray form. In some embodiments, the composition is in a lotion form. In some embodiments, the composition is applied to clothing of the subject.

In another aspect, disclosed herein is a method of preventing a mosquito from feeding on a subject comprising applying to a subject a composition in an amount effective to prevent the mosquito from feeding on the subject; wherein said composition is selected from PTG-MSQ$^{100}$, PTG-MSQ$^{200}$, Ordenone®, or mixtures thereof.

In a further aspect, disclosed herein is a method of preventing a mosquito from feeding on a subject comprising applying to a subject a composition in an amount effective to prevent the mosquito from feeding on the subject; wherein said composition is selected from:

i) a composition according to Formula I:

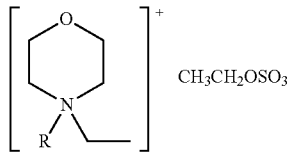

Formula I wherein R comprises a mixture of $C_{16}$-$C_{18}$ unsubstituted alkyl and $C_{16}$-$C_{18}$ unsubstituted alkenyl groups;

ii) a composition comprising betaine, sodium citrate, isopropylamine dodecylbenzene sulfonate, alcohol ethoxylate, and water;

iii) a composition comprising a water-based deodorizing agent having semi-rigid, concave molecular structures which capture odor-causing molecules;

or mixtures thereof.

In one aspect, disclosed herein is a method of reducing or preventing the transmission of a mosquito-borne pathogen, comprising applying to a subject a composition in an amount effective to reduce or prevent the transmission of a mosquito-borne pathogen; wherein said composition is selected from PTG-MSQ$^{100}$, PTG-MSQ$^{200}$, Ordenone®, or mixtures thereof.

BRIEF DESCRIPTION OF THE DRAWINGS

The accompanying figures, which are incorporated in and constitute a part of this specification, illustrate several aspects described below.

DETAILED DESCRIPTION

Figure 1:
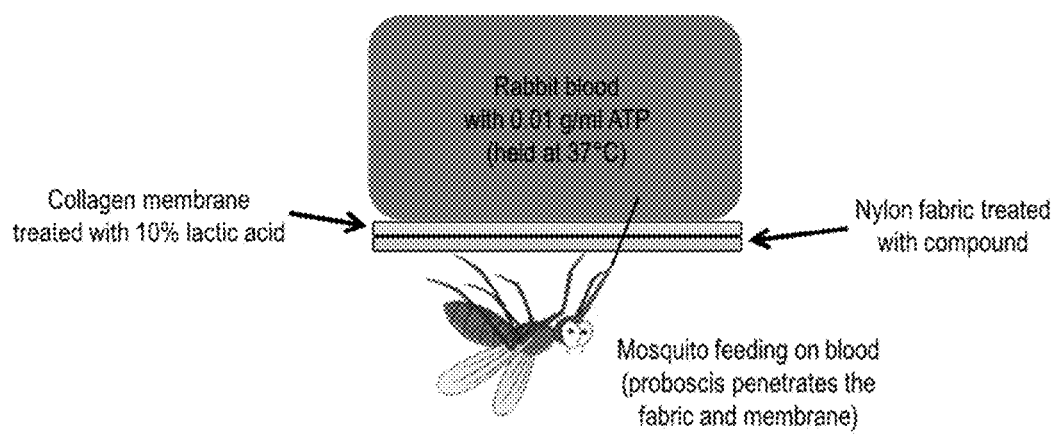
FIG. 1. Schematic illustrating bioassay used to test repellency of the compounds, which are applied to a piece of nylon fabric. For each trial, the blood is presented to a cage of 20 adult female mosquitoes for 1 h. If a mosquito does not feed, then it is considered repelled. On average, ~75% of the mosquitoes feed on the blood in the negative controls.

Disclosed herein are compounds, compositions, and methods for using deodorizing compounds and compositions for repelling insects. In some embodiments, the inventors found that the deodorizing compositions PTG-MSQ$^{100}$, PTG-MSQ$^{200}$, and Ordenone® could mask human odors and prevent mosquito bites.

Reference will now be made in detail to the embodiments of the invention, examples of which are illustrated in the drawings and the examples. This invention may, however, be embodied in many different forms and should not be construed as limited to the embodiments set forth herein.

Unless defined otherwise, all technical and scientific terms used herein have the same meaning as commonly understood to one of ordinary skill in the art to which this invention belongs. The following definitions are provided for the full understanding of terms used in this specification.

The term "alkyl" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, nonyl, decyl, dodecyl, tetradecyl, hexadecyl, eicosyl, tetracosyl, and the like.

The term "alkenyl" as used herein is a hydrocarbon group of from 2 to 24 carbon atoms with a structural formula containing at least one carbon-carbon double bond. Asymmetric structures such as $(Z^1Z^2)C=C(Z^3Z^4)$ are intended to include both the E and Z isomers. This can be presumed in structural formulae herein wherein an asymmetric alkene is present, or it can be explicitly indicated by the bond symbol C=C.

The term "mosquito" is understood to refer to any species of the 3,500 species of the insect that is commonly associated with and given the common name "mosquito". Mosquitoes span 41 insect genera, including the non-limiting examples of *Aedes, Culex,* and *Anopheles*.

The term "insect" in the context of this invention, refers to any of the arthropods that have a chitinous exoskeleton, a three-part body, and three pairs of jointed legs, i.e., any of the members of the Class Insecta. Moreover, the term "insect" is inclusive of other pestiferous arthropods of the Class Acari, which include mites and ticks. Mosquitoes are specifically included in this definition, including, but not limited to: *Aedes (Ae.) aegypti, Ae. vexans, Ae. albopictus, Ae. togoi, Ae. triseriatus, Aedes arabiensis, Culex (Cx.) quinquefasciatus, Cx. pipiens, Cx. tarsalis, Anopheles (An.) sinensis,* and *Culiseta (Cs.) inornata*.

The term "about" or "approximately" as used herein when referring to a measurable value such as an amount, a percentage, and the like, is meant to encompass variations of ±20%, ±10%, ±5%, or ±1% from the measurable value.

Deodorizing Compounds and Compositions

PTG-MSQ$^{100}$, PTG-MSQ$^{200}$, and Ordenone® have been demonstrated herein to effectively repel mosquitoes from a blood source and are thus used herein as novel mosquito repellents.

PTG-MSQ$^{100}$ (soyaethyl morpholinium ethosulfate) is a soy-derived cationic product that eliminates a wide variety of odors. The compound works by binding to volatile malodorous materials, rending them nonvolatile.

PTG-MSQ$^{100}$ is a cationic material that can work by surrounding the malodor components and not allowing them to volatilize. It is chemically attracted to anionic material and complexes with them. PTG-MSQ$^{100}$ (also referred to as PTG-D1) works well with mercaptan, amine, body, food, smoke and various other odor causing materials. It also has some antimicrobial properties that reduce the odor causing by products of bacteria. It can be used to emulsify odor causing materials. PTG-MSQ$^{100}$ has been marketed to the personal care, cosmetic and industrial applications.

PTG-MSQ$^{100}$ comprises a composition according to the following structure:

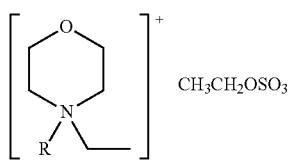

Formula I wherein R comprises a mixture of $C_{16}$-$C_{18}$ unsubstituted alkyl and $C_{16}$-$C_{18}$ unsubstituted alkenyl groups.

In some embodiments, R comprises a mixture of palmitic (16:0); linoleic (18:2 n-6); stearic (18:0); oleic (18:1 n-9); and linolenic (18:3 n-3). In some embodiments, PTG-MSQ$^{100}$ comprises 14% saturated and 81% unsaturated alkenyl groups. In some embodiments, PTG-MSQ$^{100}$ comprises about 14% saturated alkyl groups and about 81% unsaturated alkenyl groups. In some embodiments, PTG-MSQ$^{100}$ comprises 10% palmitic (16:0); 51% linoleic (18:2 n-6); 4% stearic (18:0); 23% oleic (18:1 n-9); and 7% linolenic (18:3 n-3). In some embodiments, PTG-MSQ$^{100}$ comprises about 10% palmitic (16:0); about 51% linoleic (18:2 n-6); about 4% stearic (18:0); about 23% oleic (18:1 n-9); and about 7% linolenic (18:3 n-3).

In some embodiments, PTG-MSQ$^{100}$ consists of 10% palmitic (16:0); 51% linoleic (18:2 n-6); 4% stearic (18:0); 23% oleic (18:1 n-9); and 7% linolenic (18:3 n-3). In some embodiments, PTG-MSQ$^{100}$ consists of about 10% palmitic (16:0); about 51% linoleic (18:2 n-6); about 4% stearic (18:0); about 23% oleic (18:1 n-9); and about 7% linolenic (18:3 n-3).

In some embodiments, PTG-MSQ$^{100}$ consists essentially of 10% palmitic (16:0); 51% linoleic (18:2 n-6); 4% stearic (18:0); 23% oleic (18:1 n-9); and 7% linolenic (18:3 n-3). In some embodiments, PTG-MS Q$^{100}$ consists essentially of about 10% palmitic (16:0); about 51% linoleic (18:2 n-6); about 4% stearic (18:0); about 23% oleic (18:1 n-9); and about 7% linolenic (18:3 n-3).

In some embodiments, the PTG-MSQ$^{100}$ composition is used at a concentration of 0.1-50%. In some embodiments, the PTG-MSQ$^{100}$ composition is used at a concentration of 1-15%. In some embodiments, the PTG-MSQ$^{100}$ composition is used at a concentration of 3-9%.

Some example properties of PTG-MSQ$^{100}$ include:
Antimicrobial quaternary
Biocide coadjuvant helps to improve formulation performance
Economical in use-only 0-2% use level in most formulations
Liquid, water soluble and easy to formulate
Provides emulsification properties
Provides long lasting antistatic/conditioning properties on pet hair
Vegetable based
Broad pH tolerance (pH 3-11)

Soyaethyl morpholinium ethosulfate is also described in U.S. Pat. Nos. 2,852,434, 4,851,214 and 5,180,749, all of which are incorporated herein by reference in their entirety.

PTG-MSQ$^{200}$ is an alkyl betaine ethoxysulfonate complex. The compound binds to acid or basic malodorous materials, rendering them odorless. The compound is considered environmentally friendly as it is a vegetable based complex; PTG-MSQ$^{200}$ is also safe for use in personal care and industrial applications.

PTG-MSQ$^{200}$ is a composition comprising betaine, sodium citrate, isopropylamine dodecylbenzene sulfonate, alcohol ethoxylate, and water. In some embodiments, PTG-MSQ$^{200}$ comprises betaine, sodium citrate, isopropylamine dodecylbenzene sulfonate, alcohol ethoxylate, and water. In some embodiments, PTG-MSQ$^{200}$ consists of betaine, sodium citrate, isopropylamine dodecylbenzene sulfonate, alcohol ethoxylate, and water. In some embodiments, PTG-MSQ$^{200}$ consists essentially of betaine, sodium citrate, isopropylamine dodecylbenzene sulfonate, alcohol ethoxylate, and water.

In some embodiments, PTG-MSQ$^{200}$ comprises 3-45% betaine, 1-10% sodium citrate, 1-20% isopropylamine dodecylbenzene sulfonate, 2-18% alcohol ethoxylate, and 50-90% water. In some embodiments, PTG-MSQ$^{200}$ consists of 3-45% betaine, 1-10% sodium citrate, 1-20% isopropylamine dodecylbenzene sulfonate, 2-18% alcohol ethoxylate, and 50-90% water. In some embodiments, PTG-MSQ$^{200}$ consists essentially of 3-45% betaine, 1-10% sodium citrate, 1-20% isopropylamine dodecylbenzene sulfonate, 2-18% alcohol ethoxylate, and 50-90% water.

In some embodiments, PTG-MSQ$^{200}$ comprises 3-15% betaine, 1-10% sodium citrate, 1-10% isopropylamine dodecylbenzene sulfonate, 2-10% alcohol ethoxylate, and 60-90% water. In some embodiments, PTG-MSQ$^{200}$ consists of 3-15% betaine, 1-10% sodium citrate, 1-10% isopropylamine dodecylbenzene sulfonate, 2-10% alcohol ethoxylate, and 60-90% water. In some embodiments, PTG-MSQ$^{200}$ consists essentially of 3-15% betaine, 1-10% sodium citrate, 1-10% isopropylamine dodecylbenzene sulfonate, 2-10% alcohol ethoxylate, and 60-90% water.

In some embodiments, the PTG-MSQ$^{200}$ composition is used at a concentration of 0.1-50%. In some embodiments, the PTG-MSQ$^{200}$ composition is used at a concentration of 1-50%. In some embodiments, the PTG-MSQ$^{200}$ composition is used at a concentration of 3-40%.

Some of the deodorizing mechanisms of PTG-200 include:
Ammonia (NH3) —CH2COOH+NH3→—CH2COONH4
Trimethylamine (CH3)3N—CH2COOH+(CH3)3N→—CH2COONH(CH3)3
Hydrogen Sulfide (H2S) —CH2COONa+H2S→NaHS+—CH2COOH
Methyl Mercaptan (CH3SH) —CH3COONa+CH3SH→CH3SNa+—CH2COOH Ordenone® is a registered tradename of Belle-Aire fragrances and is a semi-rigid concave molecular structure, which captures odor causing molecules. Ordenone® is an odorless deodorizing compound that permanently entraps odor molecules when sprayed into the air or directly onto the odor source, odors are encapsulated and eliminated.

Ordenone® is a composition comprising a water-based deodorizing agent having semi-rigid, concave molecular structures which capture odor-causing molecules. Ordenone® is also described in U.S. Pat. No. 6,664,254, which is hereby incorporated by reference in its entirety. In some embodiments, the Ordenone® composition is used at a concentration of 0.1-50%.

In some embodiments, the Ordenone® composition is used at a concentration of 1-20%. In some embodiments, the Ordenone® composition is used at a concentration of 10%. In some embodiments, the Ordenone® composition is used at a concentration of about 10%.

An additional deodorizer compound that can be used in the methods disclosed herein includes zinc ricinoleate.

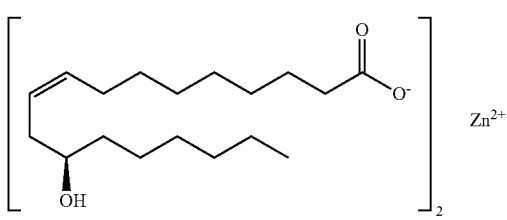

Zinc ricinoleate can be used at levels between 0-100% active in both liquid and powdered forms. Zinc ricinoleate is the zinc salt of ricinoleic acid, a major fatty acid found in castor oil. It is used in many deodorants as an odor-adsorbing agent.

Methods

In one aspect, disclosed herein is a method of repelling an insect, comprising applying to a subject a composition in an amount effective to repel said insect; wherein said composition is selected from PTG-MSQ$^{100}$, PTG-MSQ$^{200}$, Ordenone®, or mixtures thereof.

In one aspect, disclosed herein is a method of repelling an insect, comprising applying to a subject a composition in an amount effective to repel said insect; wherein said composition is selected from:

i) a composition according to Formula I:

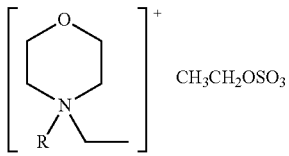

Formula I wherein R comprises a mixture of $C_{16}$-$C_{18}$ unsubstituted alkyl and $C_{16}$-$C_{18}$ unsubstituted alkenyl groups;

ii) a composition comprising betaine, sodium citrate, isopropylamine dodecylbenzene sulfonate, alcohol ethoxylate, and water;

iii) a composition comprising a water-based deodorizing agent having semi-rigid, concave molecular structures which capture odor-causing molecules;

or mixtures thereof.

In some embodiments, the composition is PTG-MSQ$^{100}$, which is a composition according to Formula I:

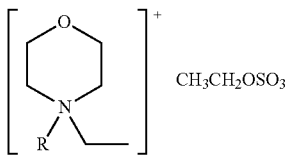

Formula I wherein R comprises a mixture of $C_{16}$-$C_{18}$ unsubstituted alkyl and $C_{16}$-$C_{18}$ unsubstituted alkenyl groups.

In some embodiments, the PTG-MSQ$^{100}$ composition is used at a concentration of 1-15%. In some embodiments, the PTG-MSQ$^{100}$ composition is used at a concentration of 3-9%.

In some embodiments, the composition is PTG-MSQ$^{200}$, which is a composition comprising betaine, sodium citrate, isopropylamine dodecylbenzene sulfonate, alcohol ethoxylate, and water.

In some embodiments, the PTG-MSQ$^{200}$ composition is used at a concentration of 1-50%. In some embodiments, the PTG-MSQ$^{200}$ composition is used at a concentration of 3-40%.

In some embodiments, the composition is Ordenone®, which is a composition comprising a water-based deodorizing agent having semi-rigid, concave molecular structures which capture odor-causing molecules.

In some embodiments, the Ordenone® composition is used at a concentration of 1-20%. In some embodiments, the Ordenone® composition is used at a concentration of 10%. In some embodiments, the Ordenone® composition is used at a concentration of about 10%.

In some embodiments, the insect (for example, arthropod) is selected from the group consisting of mosquitoes, fleas, and ticks. In some embodiments, the insect is a mosquito. In some embodiments, the mosquito is selected from an *Aedes*, *Culex*, or *Anopheles* mosquito.

In some embodiments, the subject is a human. In some embodiments, the composition is in a spray form. In some embodiments, the composition is in a lotion form. In some embodiments, the composition is applied to clothing of the subject.

In another aspect, disclosed herein is a method of preventing a mosquito from feeding on a subject comprising applying to a subject a composition in an amount effective to prevent the mosquito from feeding on the subject; wherein said composition is selected from PTG-MSQ$^{100}$, PTG-MSQ$^{200}$, Ordenone®, or mixtures thereof.

In a further aspect, disclosed herein is a method of preventing a mosquito from feeding on a subject comprising applying to a subject a composition in an amount effective to prevent the mosquito from feeding on the subject; wherein said composition is selected from:

i) a composition according to Formula I:

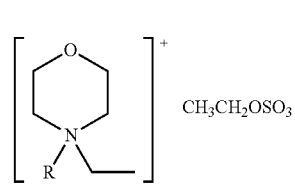

Formula I wherein R comprises a mixture of $C_{16}$-$C_{18}$ unsubstituted alkyl and $C_{16}$-$C_{18}$ unsubstituted alkenyl groups;

ii) a composition comprising betaine, sodium citrate, isopropylamine dodecylbenzene sulfonate, alcohol ethoxylate, and water;

iii) a composition comprising a water-based deodorizing agent having semi-rigid, concave molecular structures which capture odor-causing molecules;

or mixtures thereof.

In some embodiments, the composition is PTG-MSQ$^{100}$, which is a composition according to Formula I:

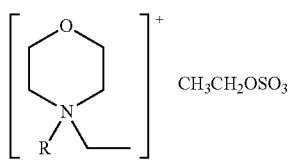

Formula I wherein R comprises a mixture of $C_{16}$-$C_{18}$ unsubstituted alkyl and $C_{16}$-$C_{18}$ unsubstituted alkenyl groups.

In some embodiments, the PTG-MSQ$^{100}$ composition is used at a concentration of 1-15%. In some embodiments, the PTG-MSQ$^{100}$ composition is used at a concentration of 3-9%.

In some embodiments, the composition is PTG-MSQ$^{200}$, which is a composition comprising betaine, sodium citrate, isopropylamine dodecylbenzene sulfonate, alcohol ethoxylate, and water.

In some embodiments, the PTG-MSQ$^{200}$ composition is used at a concentration of 1-50%. In some embodiments, the PTG-MSQ$^{200}$ composition is used at a concentration of 3-40%.

In some embodiments, the composition is Ordenone®, which is a composition comprising a water-based deodorizing agent having semi-rigid, concave molecular structures which capture odor-causing molecules.

In some embodiments, the Ordenone® composition is used at a concentration of 1-20%. In some embodiments, the Ordenone® composition is used at a concentration of 10%. In some embodiments, the Ordenone® composition is used at a concentration of about 10%.

In some embodiments, the insect (for example, arthropod) is selected from the group consisting of mosquitoes, fleas, and ticks. In some embodiments, the insect is a mosquito. In some embodiments, the mosquito is selected from an *Aedes, Culex,* or *Anopheles* mosquito.

In some embodiments, the subject is a human. In some embodiments, the composition is in a spray form. In some embodiments, the composition is in a lotion form. In some embodiments, the composition is applied to clothing of the subject.

In one aspect, disclosed herein is a method of reducing or preventing the transmission of a mosquito-borne pathogen, comprising applying to a subject a composition in an amount effective to reduce or prevent the transmission of a mosquito-borne pathogen; wherein said composition is selected from PTG-MSQ$^{100}$, PTG-MSQ$^{200}$, Ordenone®, or mixtures thereof.

Arthropods, Mosquitoes, and Pathogens

Disclosed herein are deodorizing compounds and compositions that repel adult female yellow fever mosquitoes (*Aedes aegypti*), which are the primary vectors of the viruses that cause chikungunya, dengue, yellow, and Zika fevers in humans.

Further disclosed herein are methods according to the invention wherein the insect is selected from the group consisting of mosquitoes (*Aedes* spp., *Anopheles* spp., *Culex* spp.), flies, sand flies, tsetse flies, black flies, lice, midges, fleas, ticks, bed bugs, mites, and triatomine bugs. In some embodiments, the insect is a mosquito, such as those selected from the group consisting of, for example, *Aedes* (*Ae.*) *aegypti, Ae. vexans, Ae. albopictus, Ae. togoi, Ae. triseriatus, Aedes arabiensis, Aedes polynesiensis, Culex* (*Cx.*) *quinquefasciatus, Cx. pipiens, Cx. tarsalis, Anopheles* (*An.*) *sinensis, Anopheles gambiae,* and *Culiseta* (*Cs.*) *inornata.* In one embodiment, the insect is an arthropod. In one embodiment, the arthropod is a mosquito. In one embodiment, the mosquito is selected from the genera consisting of *Aedes, Culex* and *Anopheles.*

In some embodiments, the insects can be disease vectors carrying a pathogen (virus, bacterium or parasite) which causes disease in mammals. Examples of vector-borne diseases can include but are not limited to Dengue fever, Zika virus, chikungunya, Rift Valley fever, yellow fever, malaria, Japanese encephalitis, lymphatic filariasis, West Nile fever, leishmaniasis, sandfly fever, lyme disease, plague, tularaemia, Chagas disease, and onchocerciasis, or any insect-borne disease. In one embodiment, the pathogen is selected from dengue virus, Zika virus, a malaria parasite (*Plasmodium* genus), West Nile virus, yellow fever virus, chikungunya virus, Japanese encephalitis, St. Louis encephalitis and Western and Eastern Equine Encephalitis viruses.

In some aspects, the composition includes one or more of mineral oil, glycerol, or a diluent that provides viscosity modifying properties. The composition can be formulated to be suitable for application as an aerosol, fog, mist, spray, vapor, ultra-low volume spray (ULV), surface contact treatment, or a combination thereof.

In other aspects, a method for controlling insects is provided, in which a population of insects, such as mosquitoes, is contacted with an effective amount of a composition described in this specification. The population of insects can be controlled by topically applying the composition to the population in an amount sufficient to kill at least 25%, 50%, or any proportion disclosed in this specification of the population.

Additional Composition Components

Compositions, as described herein, comprising PTG-MSQ$^{100}$, PTG-MSQ$^{200}$, or Ordenone® and an excipient of some sort may be useful in a variety of applications. For example, compositions comprising PTG-MSQ$^{100}$, PTG-MSQ$^{200}$, and Ordenone® and an excipient can be useful for the repelling insects (including mosquitoes) and can be useful for preventing or reducing vector-borne diseases.

"Excipients" include any and all solvents, diluents or other liquid vehicles, dispersion or suspension aids, surface active agents, isotonic agents, thickening or emulsifying agents, preservatives, solid binders, lubricants and the like, as suited to the particular dosage form desired. General considerations in formulation and/or manufacture can be found, for example, in *Remington's Pharmaceutical Sciences,* Sixteenth Edition, E. W. Martin (Mack Publishing Co., Easton, Pa., 1980), and *Remington: The Science and Practice of Pharmacy,* 21st Edition (Lippincott Williams & Wilkins, 2005).

Exemplary excipients include, but are not limited to, any non-toxic, inert solid, semi-solid or liquid filler, diluent, encapsulating material or formulation auxiliary of any type. Some examples of materials which can serve as excipients include, but are not limited to, sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate; agar; detergents such as Tween 80; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. As would be appreciated by one of skill in this art, the excipients may be chosen based on what the composition is useful for. For example, with a composition, the choice of the excipient will depend on the route of administration, the agent being delivered, time course of delivery of the agent, etc.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof.

Exemplary granulating and/or dispersing agents include potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

Exemplary surface active agents and/or emulsifiers include natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof. In some embodiments, the composition comprises dimethyl isosorbide.

Exemplary binding agents include starch (e.g. cornstarch and starch paste), gelatin, sugars (e.g. sucrose, glucose, dextrose, dextrin, molasses, lactose, lactitol, mannitol, etc.), natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, etc., and/or combinations thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

Additionally, the composition may further comprise a polymer. Exemplary polymers contemplated herein include, but are not limited to, cellulosic polymers and copolymers, for example, cellulose ethers such as methylcellulose (MC), hydroxyethylcellulose (HEC), hydroxypropyl cellulose (HPC), hydroxypropyl methyl cellulose (HPMC), methylhydroxyethylcellulose (MHEC), methylhydroxypropylcellulose (MHPC), carboxymethyl cellulose (CMC) and its various salts, including, e.g., the sodium salt, hydroxyethylcarboxymethylcellulose (HECMC) and its various salts, carboxymethylhydroxyethylcellulose (CMHEC) and its various salts, other polysaccharides and polysaccharide derivatives such as starch, dextran, dextran derivatives, chitosan, and alginic acid and its various salts, carageenan, various gums, including xanthan gum, guar gum, gum arabic, gum karaya, gum ghatti, konjac and gum tragacanth, glycosaminoglycans and proteoglycans such as hyaluronic acid and its salts, proteins such as gelatin, collagen, albumin, and fibrin, other polymers, for example, polyhydroxyacids such as polylactide, polyglycolide, polyl(lactide-co-glycolide) and poly(.epsilon.-caprolactone-co-glycolide)-, carboxyvinyl polymers and their salts (e.g., carbomer), polyvinylpyrrolidone (PVP), polyacrylic acid and its salts, polyacrylamide, polyacilic acid/acrylamide copolymer, polyalkylene oxides such as polyethylene oxide, polypropylene oxide, poly(ethylene oxide-propylene oxide), and a Pluronic polymer, polyoxyethylene (polyethylene glycol), polyanhydrides, polyvinylalchol, polyethyleneamine and polypyrridine, polyethylene glycol (PEG) polymers, such as PEGylated lipids (e.g., PEG-stearate, 1,2-Distearoyl-sn-glycero-3-Phosphoethanolamine-N-[Methoxy(Polyethylene glycol)-1000], 1,2-Distearoyl-sn-glycero-3-Phosphoethanolamine-N-[Methoxy(Polyethylene glycol)-2000], and 1,2-Distearoyl-sn-glycero-3-Phosphoethanolamine-N-[Methoxy(Polyethylene glycol)-5000]), copolymers and salts thereof.

Additionally, the composition may further comprise an emulsifying agent. Exemplary emulsifying agents include, but are not limited to, a polyethylene glycol (PEG), a polypropylene glycol, a polyvinyl alcohol, a poly-N-vinyl pyrrolidone and copolymers thereof, poloxamer nonionic surfactants, neutral water-soluble polysaccharides (e.g., dextran, Ficoll, celluloses), non-cationic poly(meth)acrylates, non-cationic polyacrylates, such as poly(meth)acrylic acid, and esters amide and hydroxyalkyl amides thereof, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof. In certain embodiments, the emulsifying agent is cholesterol.

Liquid compositions include emulsions, microemulsions, solutions, suspensions, syrups, and elixirs. In addition to the active compound, the liquid composition may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Compositions for topical or transdermal administration include ointments, pastes, creams, lotions, gels, powders, solutions, sprays, inhalants, or patches. The active compound is admixed with an excipient and any needed preservatives or buffers as may be required.

The ointments, pastes, creams, and gels may contain, in addition to the active compound, excipients such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to the active compound, excipients such as lactose, talc, silicic acid, aluminum hydroxide, calcium silicates, and polyamide powder, or mixtures of these substances. Sprays can additionally contain customary propellants such as chlorofluorohydrocarbons.

The active ingredient may be administered in such amounts, time, and route deemed necessary in order to achieve the desired result. The exact amount of the active ingredient will vary from subject to subject, depending on the species, age, and general condition of the subject, the severity of the infection, the particular active ingredient, its mode of administration, its mode of activity, and the like. The active ingredient, whether the active compound itself, or the active compound in combination with an agent, is preferably formulated in dosage unit form for ease of administration and uniformity of dosage. It will be understood, however, that the total daily usage of the active ingredient will be decided by the attending physician within the scope of sound medical judgment. The specific therapeutically effective dose level for any particular subject will depend upon a variety of factors including the disorder being treated and the severity of the disorder; the activity of the active ingredient employed; the specific composition employed; the age, body weight, general health, sex and diet of the patient; the time of administration, route of administration, and rate of excretion of the specific active ingredient employed; the duration of the treatment; drugs used in combination or coincidental with the specific active ingredient employed; and like factors well known in the medical arts.

The exact amount of an active ingredient required to achieve a therapeutically or prophylactically effective amount will vary from subject to subject, depending on species, age, and general condition of a subject, severity of the side effects or disorder, identity of the particular compound(s), mode of administration, and the like. The amount to be administered to, for example, a child or an adolescent can be determined by a medical practitioner or person skilled in the art and can be lower or the same as that administered to an adult.

Further optionally, the present composition may have one or more of the following additional ingredients: anesthetics, anti-allergenics, antifungals, anti-inflammatories, antiseptics, chelating agents, colorants, depigmenting agents, emollients, emulsifiers, exfollients, fragrances, humectants, lubricants, moisturizers, pharmaceutical agents, preservatives, skin penetration enhancers, stabilizers, surfactants, thickeners, viscosity modifiers, vitamins or any combinations of these ingredients. In some embodiments, the skin penetration enhancer is dimethyl isosorbide.

EXAMPLES

The following examples are set forth below to illustrate the compounds, compositions, methods, and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Example 1. Analysis of Deodorizing Compounds for Repelling Insects

Mosquitoes are vectors of several medically-important arboviruses and parasites that are currently emerging and/or re-emerging around the globe, such as dengue fever, chikungunya fever, malaria, yellow fever, and Zika virus. Vaccines for these diseases have not been developed (e.g., Zika), are not widely-available (e.g., dengue), or are limited in their supply (e.g., yellow fever). Thus, avoiding mosquito bites is the primary strategy to preventing transmission of these diseases. While the application of insecticides and elimination of larval breeding sites are key components to managing mosquito populations, the use of repellents provides an important level of personal protection to minimize the chances of mosquito bites. However, the list of EPA-registered repellents that are recommended by the CDC for preventing mosquito bites is currently limited to N,N-Diethyl-meta-toluamide (DEET), picaridin, para-methane-diol (oil of lemon eucalyptus), and IR3535. Moreover, DEET, which is considered the "gold standard" for a repellent, has some important drawbacks: it can dissolve plastics and mosquitoes can become resistant to it. Thus, new molecules are needed to embellish the diversity of active ingredients for developing novel mosquito repellents and help limit the spread of mosquito-borne diseases caused by mosquito-borne pathogens.

One source of chemicals for developing new repellents is the drug, cosmetic, and personal hygiene industry, where compounds have already been approved and shown to be safe for human use. The current example exploits this source of chemicals to result in the novel use of deodorizing compounds as mosquito repellents. In brief, three deodorizing agents commonly-used in household goods (PTG-MSQ$^{100}$, PTG-MSQ$^{200}$, Ordenone®) have been demonstrated to effectively repel mosquitoes from a blood source, suggesting that they have potential for development into novel mosquito repellents. In particular, it was shown that these compounds repel adult female yellow fever mosquitoes (*Aedes aegypti*), which are the primary vectors of the viruses that cause chikungunya, dengue, yellow, and Zika fevers in humans. These compounds and compositions can also work on a wide variety of mosquito species and on other blood-feeding pests/vectors of medical and veterinary importance, such as flea, ticks, and bed bugs.

PTG-MSQ$^{100}$ (soyaethyl morpholinium ethosulfate) is a soy-derived cationic product that eliminates a wide variety of odors. The compound can work by binding to volatile malodorous materials, rending them nonvolatile. PTG-MSQ$^{200}$ is an alkyl betaine ethoxysulfonate complex. The compound can bind to acid or basic malodorous materials, rendering them odorless. The compound is considered environmentally friendly as it is a vegetable based complex; PTG-MSQ200 is also safe for use in personal care and industrial applications.

Ordenone® is a registered tradename of Belle-Aire fragrances (http://www.belleairecreations.com/fragrance/) and is a semi-rigid concave molecular structure, which captures odor causing molecules.

In this example, a blood-feeding bioassay was used to test the efficacy of each compound to repel mosquitoes from feeding on a blood source. In brief, cages of twenty mosquitoes (adult females) were starved for 24 hours before being allowed to feed on a membrane feeder (Hemotek) containing defibrinated rabbit blood. After 1 hour, the mosquitoes were immobilized on ice and the number of individuals with blood in their abdomen was counted. The membrane feeder maintains the blood at a constant temperature of 37° C. (human body temperature) and is covered with a collagen membrane that mimics human skin. Mosquitoes pierce through the collagen membrane with their proboscis to obtain the blood (FIG. 1). To make the blood source attractive to mosquitoes, 10% lactic acid (a known mosquito attractant) is applied to the collagen membrane with a cotton wick and 0.01 g/ml of adenosine triphosphate (a feeding stimulant) is added to the blood. The blood feeding experiments took place in a rearing chamber held at 28° C. (80% relative humidity), and occurred around the same time each day (~1-3 PM).

To determine if a particular compound exhibited repellent effects, the compound was diluted in 100% acetone and 250 µl was applied to a small piece of nylon fabric covering the collagen membrane (FIG. 1). As a negative control, water was diluted to a similar degree in 100% acetone and applied to the membrane. As a positive control and a reference point, 1% DEET (dissolved in acetone) was applied to the membrane. The mean feeding rate of the negative controls was 74.5±2.35% (N=44). Repellency efficacy for the compounds was calculated by first normalizing the feeding rates to that of the negative control and then determining the % inhibition of the feeding rate with the compound relative to the negative control.

Figure 2:
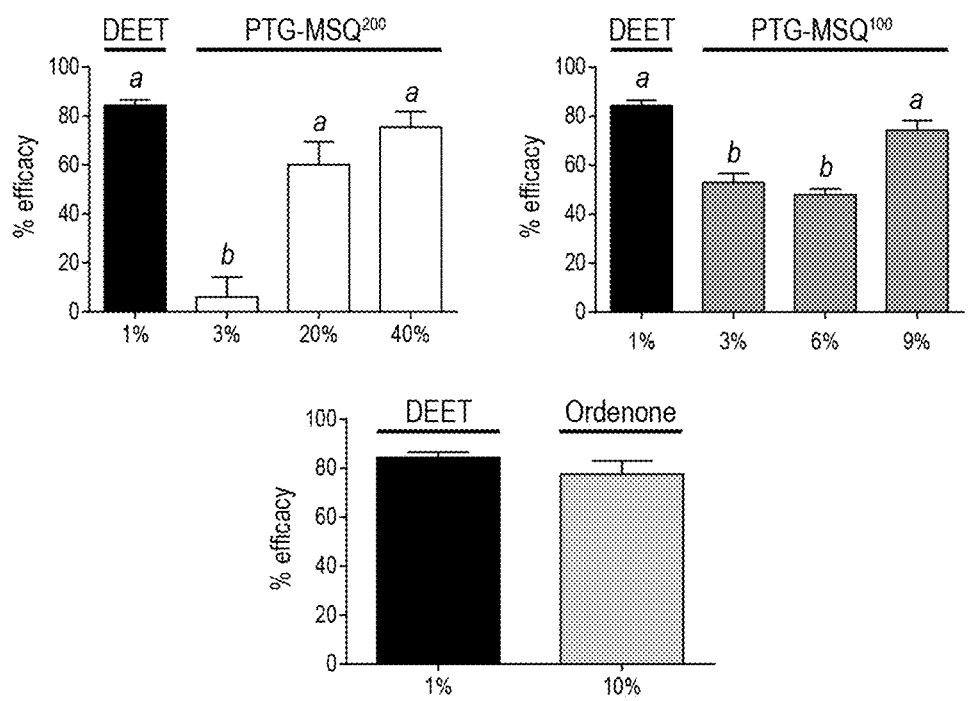
FIG. 2. Repellent efficacy of PTG compounds and Ordenone® vs. 1% DEET. Values are means±SEM; N=6 for each data set except for 1% DEET (N=3) and 3% PTG-MSQ$^{100}$ (N=5). Lower-case letters indicate statistical categorization of the means as determined by a one-way ANOVA with a Newman-Keuls posttest (P<0.05). The efficacy of 1% DEET and 10% Ordenone® were not significantly different from one another.

The repellent efficacy of each compound tested relative to 1% DEET is shown in FIG. 2. In brief, the efficacy of PTG-MSQ$^{200}$ is statistically similar to that of DEET when applied to the nylon fabric at a concentration of 20% or 40%. The efficacy of PTG-MSQ$^{100}$ is statistically similar to that of DEET when applied to the nylon fabric at a concentration of 9%. Ordenone® was only tested at a concentration of 10%, where it was statistically similar to DEET. Thus, each compound tested is able to reach a similar efficacy as DEET, albeit at different concentrations. PTG-MSQ$^{200}$ may require higher concentrations that PTG-MSQ$^{100}$ to reach similar efficacy, because the concentration of the active ingredient in PTG-MSQ$^{200}$ is 15% vs. 35% in PTG-MSQ$^{100}$. The concentration of the active ingredient in Ordenone® is unknown.

While the compounds in this example were tested against *Aedes aegypti*, these compounds can also be effective against other blood-feeding arthropods that use odors as cues for finding human hosts (e.g., fleas, ticks, bed bugs).

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

We claim:

1. A method of repelling an insect, comprising applying to a subject a composition in an amount effective to repel said insect; wherein said composition comprises Formula I:

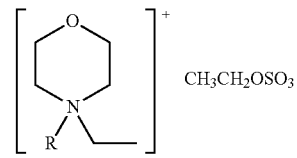

Formula I wherein R comprises a mixture of $C_{16}$-$C_{18}$ unsubstituted alkyl and $C_{16}$-$C_{18}$ unsubstituted alkenyl groups; and
wherein the composition does not comprise thymol or carvacrol.

2. The method of claim 1, wherein the composition is applied at a concentration of 1-15%.

3. The method of claim 2, wherein the composition is applied at a concentration of 3-9%.

4. The method of claim 1, wherein the insect is a mosquito.

5. The method of claim 4, wherein the mosquito is selected from an *Aedes, Culex*, or *Anopheles* mosquito.

6. The method of claim 1, wherein the subject is a human.

* * * * *